United States Patent [19]

Lassiter

[11] Patent Number: 4,964,153
[45] Date of Patent: Oct. 16, 1990

[54] PATIENT SUPPORT STRUCTURE FOR PERFORMING DEFECOGRAPHY STUDIES

[75] Inventor: Donnie A. Lassiter, Greenville, N.C.

[73] Assignee: Pitt County Memorial Hospital, Greenville, N.C.

[21] Appl. No.: 299,453

[22] Filed: Jan. 23, 1989

[51] Int. Cl.$^5$ .............................................. H05G 1/00
[52] U.S. Cl. ..................................... 378/208; 378/68; 4/456
[58] Field of Search .................... 378/18, 68, 177–180, 378/195–196, 208–209; 4/456, 245; 5/455

[56] References Cited

U.S. PATENT DOCUMENTS

| 1,442,027 | 1/1923 | Levenson | 378/208 |
|---|---|---|---|
| 1,967,598 | 7/1934 | Stanley | 4/456 |
| 2,671,226 | 3/1954 | Lychenheim | 4/456 |
| 2,678,396 | 5/1954 | Dunn | 378/180 |
| 2,790,083 | 4/1957 | Snawder et al. | 378/178 |
| 3,082,322 | 3/1963 | Koerner et al. | 378/196 |
| 3,728,744 | 4/1973 | Kimbro, Jr. et al. | 4/456 |
| 4,207,633 | 6/1980 | Smith et al. | 4/456 |

Primary Examiner—Carolyn E. Fields
Assistant Examiner—David P. Porta
Attorney, Agent, or Firm—Rhodes, Coats & Bennett

[57] ABSTRACT

The present invention entails a patient support structure designed to be utilized in conjunction with a cradle of a conventional x-ray machine. In particular, the patient support structure includes a box type base structure that includes a top central opening and a clear fluid filled buttock support mounted atop the central opening. While the patient sets on the patient support structure an infusion line designed to carry a radiopaque medium is threaded through the structure and inserted into the anus of the patient.

4 Claims, 4 Drawing Sheets

PATIENT SUPPORT STRUCTURE FOR PERFORMING DEFECOGRAPHY STUDIES

FIELD OF THE INVENTION

The present invention relates to medical appliances and the general field of surgery, and more particularly to a patient support structure designed to be utilized in conjunction with a conventional x-ray machine for the purpose of conducting defecography studies.

BACKGROUND OF THE INVENTION

Physicians have difficulty in adequately diagnosing rectum problems relating generally to defecation and rectal incontinence. In studying the rectum and defecation related problems, a physician will ordinarily observe approximately the final seven inches of the rectum immediately above the sphincter. The sphincter controls the terminal outlet of the rectum, that is that area referred to as the anus. Typically, defecation related problems include the patient's inability to completely empty his or her bowel and rectal ulcerations. Often in studying defecation related problems, the examining physician will find that the rectum is "pouching" or protruding into other areas of the lower abdomen, or is in fact closing in on itself. Some of the protrusions include rectal intussusception, rectocoele (pouching into the vagina), anorectocoele and descensis.

One of the principal reasons for the difficulty in diagnosing defecation related problems is that the patient is traditionally viewed in a simple horizontal lying position. The obvious shortcoming to this observation is that with respect to defecation related problems that the patient is not in a defecating position nor is the patient attempting to empty his or her bowel. Thus, it is quite difficult to diagnose a defecation related problem when the patient is not even in a conventional defecating position and when the patient is not straining or otherwise in the act of emptying his or her bowel.

Recently, it has been suggested that such defecation related problems can best be diagnosed and studied while the patient is sitting in a conventional defecating position and is actually attempting a bowel movement.

Although it has been known that defecation related problems can be best observed and studied while the patient is in a conventional defecating position and is in fact attempting or simulating defecation, there has been little effort at designing a support structure that will:

(1) appropriately support the patient in a conventional defecating position, (2) allow the patient to in fact defecate or simulate defecation, and (3) position the rectum about the support structure such that a clear and well-defined defecography can be obtained.

SUMMARY AND OBJECTS OF THE INVENTION

The present invention entails a support apparatus for supporting a patient in an upright conventional defecating position while a defecography observation and study is being performed. The support apparatus of the present invention is designed to receive the patient and to position the patient in an environment that is similar to a commode and bathroom environment. In particular, the apparatus of the present invention supports the patient in a sitting position and provides access to the rectum area that enables a particular radiopaque medium to be injected up through the patient's anus into the lower area of the rectum.

In addition, the support structure is provided with a clear fluid filled annular support that encircles the patient's buttocks such that a lower portion of the patient's rectum lies generally within the confines of the clear fluid filled annular support structure.

It is therefore an object of the present invention to provide a support structure for supporting a patient in a conventional defecating position while defecography observations and studies are being made.

Still a further object of the present invention resides in the provision of a patient support structure for supporting a patient in a conventional defecating position while enabling the patient to actually simulate a bowel movement for purposes of providing a defecography image of the patient's rectum area.

Another object of the present invention resides in the provision of a support structure of the character referred to above that is compatible with conventional x-ray machines.

Another object of the present invention resides in the provision of a support structure for preforming defecography studies which is provided with provisions for enabling a radiopaque medium to be channelled through the support structure and into the rectum area of a patient.

Still a further object of the present invention is to provide a support structure of the character referred to above which is relatively simple in design and which can be manufactured easily.

Other objects and advantages of the present invention will become apparent and obvious from a study of the following description and the accompanying drawings which are merely illustrative of such invention.

DETAILED DESCRIPTION OF THE INVENTION

Figure 1:
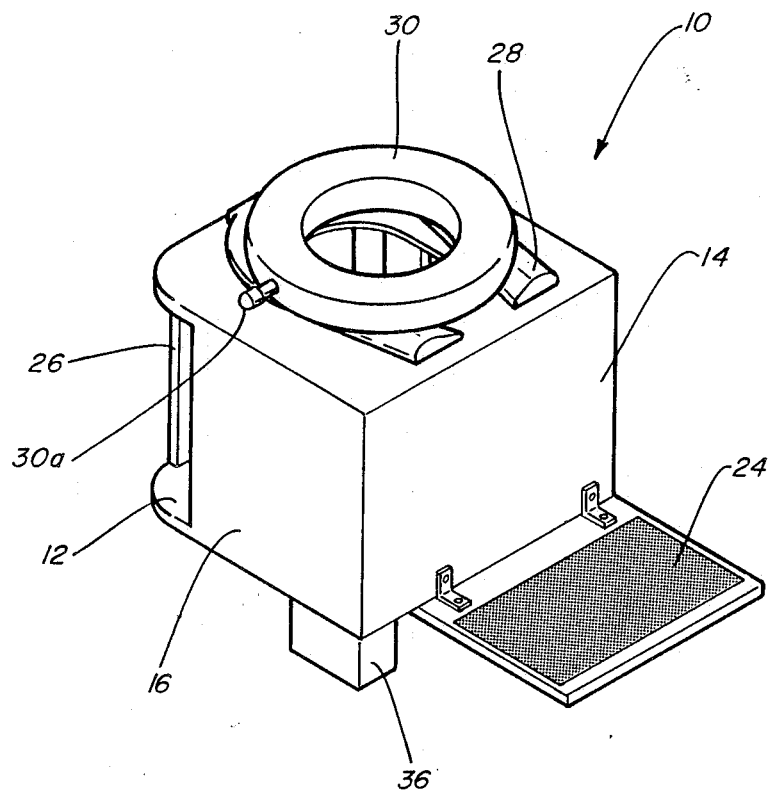
FIG. 1 is a perspective view of the patient support structure for performing defecography studies.
Figure 2:
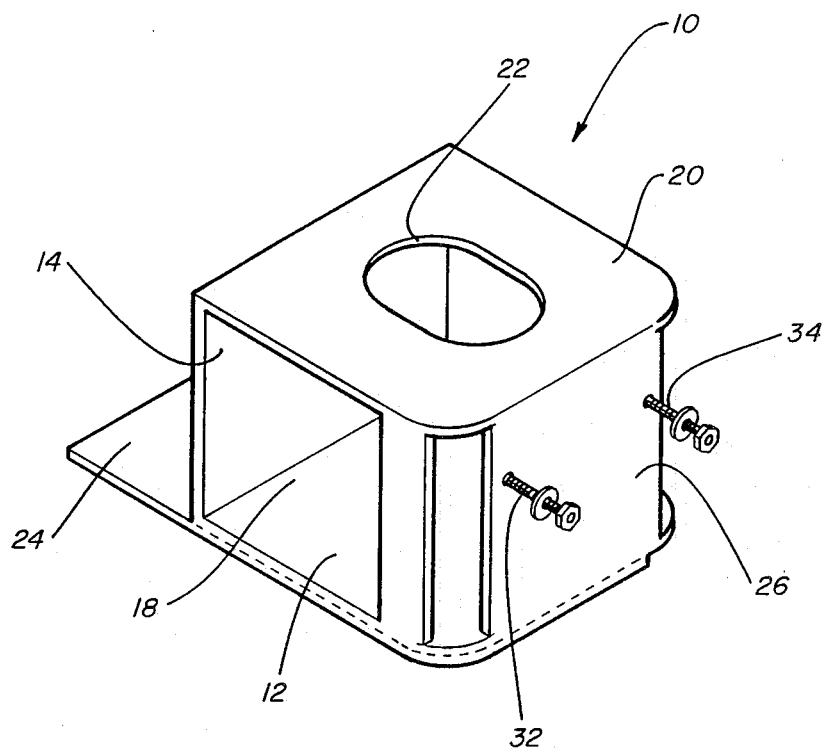
FIG. 2 is another perspective view of the patient support structure showing the back side thereof and attaching bolts for attaching the same to an x-ray machine.

With further reference to the drawings, there is shown therein a patient support structure which is indicated generally by the numeral 10. As will be understood from a reading of this disclosure, the patient support structure 10 is designed to support a patient in a sitting position while the patient is being administered an examination intended to provide a defecography image of the patient's rectum.

Turning to the patient support structure 10, it is seen that the same is a box type support structure and is designed to be received and mounted to the cradle 40 of a conventional x-ray machine. Viewing the box type base support structure it is seen that the same includes a bottom 12, a front panel 14, a closed side 16, opposite open side 18, a top panel 20 and back 26. It is appreciated that this structure defines an open internal area 19.

Figure 3:
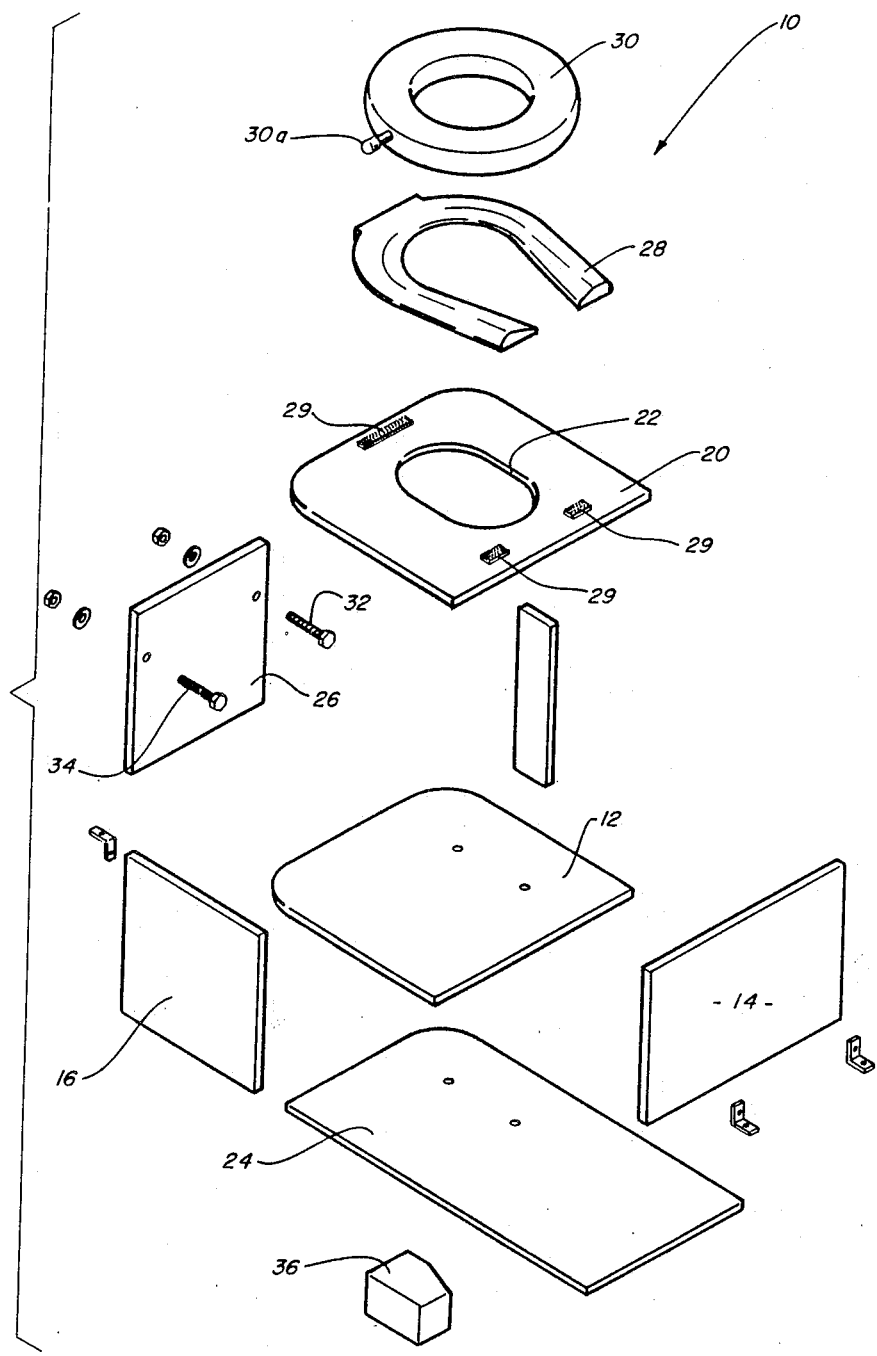
FIG. 3 is an exploded view showing the particular components of the patient support structure.

There is also provided a bottom extension 24 that may simple comprise an extension of bottom 12. But as seen in the drawings, bottom extension 24 forms a foot rest and projects outwardly from the front panel 14. It is noted that in this particular embodiment, the bottom structure is comprised of overlying panels 12 and 24 (FIG. 3).

Formed in top panel 20 is a top panel opening 22. Detachably secured to top panel 20 about top panel opening 22 is a conventional commode seat 28. As shown in the drawings, commode seat 28 is detachably mounted to the top panel 20 through a velcro attaching structure 29.

Secured atop commode seat 28 is an annular or doughnut shaped buttock support 30. Buttock support 30 is preferably formed or constructed of a plastic material and is designed to hold a clear fluid such as water. To fill the buttock support 30, there is provided a fluid inlet/outlet 38.

As seen in the drawings, and as already noted, buttock support 30 is annular in shape and defines a central opening that is generally aligned with the top panel opening 22. The buttock support 30 is designed to receive and support the buttocks of a patient while a defecography study is being performed. In particular, the central opening in the buttock support 30 is designed to receive the patient such that the area around the terminal end of the rectum or anus will lie in the plane or below the plane of the top surface of the buttock support 30.

As can be appreciated, the buttock support 30 serves a number of functions. Besides providing a generally resilient and comfortable support structure, the buttock support 30 elevates the rectum above the commode seat 28 and the box type base support structure. Because buttock support 30 includes a clear fluid medium, it is appreciated that the rectum lies in an unobstructed path with respect to the x-ray beam. Consequently, the desired observation area, that is the rectum, lies unobstructed.

Continuing to refer to the patient support structure 10 of the present invention, it is seen that the same is specifically designed to be mounted on one end of an x-ray machine cradle 40 when that cradle is oriented in a vertical position. The patient support structure 10 of the present invention is designed to be received and supported about one end of the cradle of the x-ray machine. In the case of the embodiment disclosed herein, there is provided a pair of attaching bolt assemblies 32 and 34 that project from the back panel 26 of the base support structure. These bolt assemblies 32 and 34 are designed to project into and through slots formed in the cradle itself. Consequently by screwing down on the nuts forming a part of the bolt assemblies 32 and 34 the back portion of the patient support 10 can be securely mounted to the cradle of the x-ray machine.

The embodiment disclosed herein includes a detachable stabilizing leg 36 that is particularly provided to stabilize the patient support structure 10 when the same is supported by a certain type of x-ray machine cradle. In particular, there is at least one x-ray machine cradle design where the end panel thereof is inadequate to support the bottom 12 of the patient support structure 10 and the detachable stabilizing leg 36 is utilized to project downwardly for engagement with a lower level or adjacent support structure.

Figure 4:
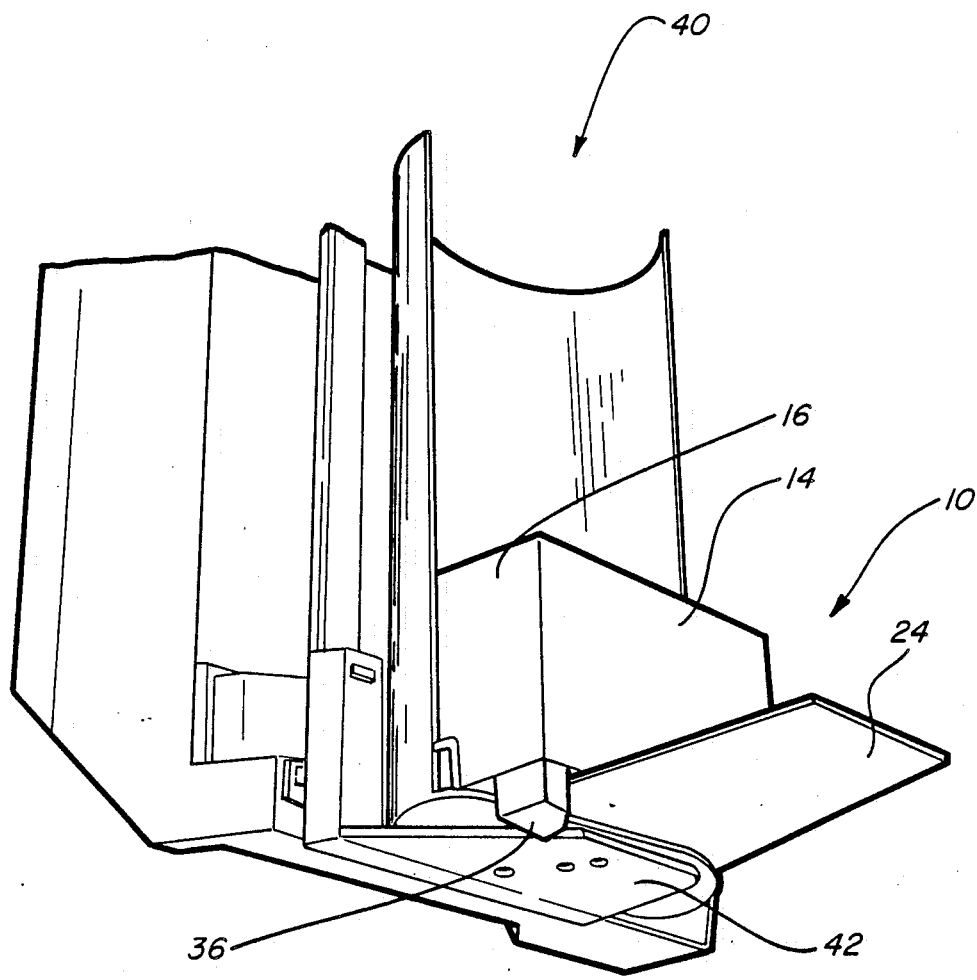
FIG. 4 is a fragmentary perspective view illustrating the patient support structure mounted to the cradle of an x-ray machine.

Turning to FIG. 4, there is shown therein an x-ray machine cradle, indicated generally by the numeral 40. This type of cradle 40 includes a relatively small end panel 42 that does not completely cover the major portion of the bottom 12 of the patient support structure 10 and therefore the detachable leg 36 is needed for stability. In FIG. 4, the detachable leg 36 engages a lower end portion of the cradle 40 that has been removed to better illustrate how end panel 42 supports the patient support structure 10.

In use, the patient support structure 10 is mounted to the cradle 40 of an x-ray machine and the cradle is oriented in an upright vertical position. The patient then sits on the buttock support 30 while his or her feet are supported on the foot support 24. At this time, the defecography study can commence.

In carrying out the examination, a relatively thick radiopaque medium formulated to simulate a stool is injected up through the patient's anus into his or her rectum. Typically, the radiopaque medium is contained within a cartridge that is designed to fit into an application gun. Extending from the cartridge is a line, such as flexible tubing, that includes a terminal tip portion designed to be inserted into the anus of the patient.

To carry out this procedure, the flexible line is threaded through the side opening 18 of the patient support structure 10. The terminal tip of the line is extended upwardly through the top panel opening 20 and through the buttock support 30 into the anus of the patient.

While the test or observation is being performed, a bedpan or the like can be placed on the bottom 12 to catch expelled medium or waste from the patient.

During examination x-rays will be taken of the rectum while the patient is in some form of a defecating mode. That is, the patient will be acting or straining to cause a bowel movement. While the patient is so acting x-ray beams will be directed through the buttock support 30 the patient's rectum for capturing an image of the rectum while the patient is straining or attempting to cause a bowel movement.

It is appreciated that the support structure 10 of the present invention is totally compatible with the test and procedure performed for obtaining the defecography study. The support structure simulates a bathroom or commode environment while its design is completely compatible with the cradle of a conventional x-ray machine. Also the support structure 10 accommodates the infusion device that is utilized to inject the radiopaque medium into the rectum.

The present invention may, of course, carried out in other specific ways than those herein set forth without parting from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A radiological support structure for supporting a patient in a conventional defecating position for performing defecography studies comprising:
   (a) base support structure having a top with a central opening therein, a surrounding side wall structure, and an internal open area defined below the top and within the surrounding side wall structure;
   (b) an access opening formed in the base support structure comprising mean for channelling a radiopaque medium through the internal open area of the base support structure; and (c) a clear fluid filled annular buttock support disposed over the central opening of the top of the base structure for receiving and supporting the anus of the patient such that portions of the patient's rectum lie within the support structure and wherein the clear fluid filled buttock support structure elevates and supports the rectum in a position for simulating defecation.

2. The radiological support structure for forming defecography studies of claim 1 including a commode seat structure interposed between the top of the base support structure and the annular buttock support.

3. The radiological support structure for performing defecography studies of claim 1 wherein the base support structure includes a bottom.

4. The radiological support structure for performing defecography studies of claim 3 further including a footrest structure projecting outwardly from the base support structure and spaced below the central opening within the top of the base support structure.

* * * * *